United States Patent [19]

Greenberg et al.

[11] Patent Number: 4,571,385

[45] Date of Patent: Feb. 18, 1986

[54] GENETIC REASSORTMENT OF ROTAVIRUSES FOR PRODUCTION OF VACCINES AND VACCINE PRECURSORS

[75] Inventors: Harry B. Greenberg, Palo Alto, Calif.; Richard G. Wyatt, Potomac, Md.; Albert Z. Kapikian; Anthony R. Kalica, both of Rockville, Md.; Karen Midthun, Sharpsburg, Md.; Robert M. Chanock, Bethesda, Md.

[73] Assignee: The United States of America as represented by the Department of Health and Human Services, Washington, D.C.

[21] Appl. No.: 508,323

[22] Filed: Jun. 27, 1983

[51] Int. Cl.⁴ .................. C12N 15/00; C12N 7/04; C12N 7/08; C12R 1/91
[52] U.S. Cl. .................. 435/172.3; 435/172.1; 435/236; 435/237; 435/948; 424/89; 424/86; 935/65; 935/111; 935/95
[58] Field of Search ............... 435/172.2, 172.3, 172.1, 435/948, 236, 237; 424/89, 86; 935/65, 95, 89, 111

[56] References Cited

U.S. PATENT DOCUMENTS 3,992,522 11/1976 Chanock et al. ............... 435/172.1
4,341,870 7/1982 Wyatt et al. ..................... 435/237

OTHER PUBLICATIONS

Kapikian et al, "Antigenic Characterization of Human and Animal Rotaviruses by Immune Adherence Hemagglutination Assay", Infection and Immunity 33(2), pp. 415-425 (1981).
Greenberg et al, "Rescue and Serotypic Characterization of Noncultivable Human Rotavirus by Gene Reassortment", Infection and Immunity 37(1), pp. 104-109 (1982).
Greenberg et al, "Rescue of Noncultivatable Human Rotavirus by Gene Reassortment during Mixed Infection", Proceedings of the National Academy of Sciences 78(1), pp. 420-424 (1981).
Kalica et al, "Genes of Human (Strain Wa) and Bovine (Strain UK) Rotavirus that Code for Neutralization and SubGroup Antigens", Virology 112, pp. 385-390 (1981).
Greenberg et al, "Serological Analysis of the Subgroup Protein of Rotavirus using Monoclonal Antibodies", Infection and Immunity 39(1), pp. 91-99 (1983).
Greenberg et al, "Production and Preliminary Characterization of Monoclonal Antibodies Directed at Two Surface Proteins . . . ", Journal of Virology 47, pp. 267-275 (1983).
McCrae et al, "Molecular Biology of Rotaviruses", Journal of Virology 39(2), pp. 490-496 (1981).
Infection and Immunity 37(1), pp. 110-115 (1982).
Virology 125, pp. 194-205 (1983).
Virology 121, pp. 288-295 (1982).
Journal of General Virology 64, pp. 313-324 (1983).

Primary Examiner—Thomas G. Wiseman
Assistant Examiner—John Edward Tarcza
Attorney, Agent, or Firm—John S. Roberts, Jr.

[57] ABSTRACT

This invention relates to processes which are used to produce, isolate, and characterize human rotavirus/animal rotavirus reassortants and to produce live attenuated vaccines and vaccine precursors. In the present strategy there is involved the new use of either (1) high titer hyperimmune antisera or (2) monoclonal antisera to select reassortants with the desired human phenotype. A point of novelty is the finding that antiserum or monoclonal antisera alone, so long as it possesses high titer neutralizing activity against only the 34-38Kd glycoprotein or of the animal parent, is sufficient to use for selection of reassortant rotaviruses with human phenotype. Also, the novel products are live attenuated vaccine precursors and vaccines.

7 Claims, No Drawings

GENETIC REASSORTMENT OF ROTAVIRUSES FOR PRODUCTION OF VACCINES AND VACCINE PRECURSORS

This invention relates to processes which are used to produce, isolate, and characterize human rotavirus/animal rotavirus reassortants and to produce live attenuated vaccines and vaccine precursors. In the present strategy there is involved the new use of either (1) high titer hyperimmune antisera or (2) monoclonal antisera to select reassortants with the desired human phenotype. A point of novelty is the finding that antiserum alone or monoclonal antibody so long as it possesses high titer neutralizing activity against only the 34–38Kd glycoprotein of the animal parent, is sufficient to use for selection of reassortant rotaviruses with human phenotype. Also, the novel products are live attenuated vaccine precursors and vaccines. It is noted that reassortant viruses (using wild type animal virus) as vaccines have at least two advantages over other reassortant vaccines using a temperature-sensitive animal virus as a parent: (1) they are potentially more stable than viruses with attenuating lesions produced by mutagenesis of various forms and (2) fewer human rotavirus genes are generally present in reassortants prepared using non-temperature sensitive animal rotavirus parents than using temperature sensitive rotavirus.

Rotaviruses are an important cause of infantile diarrhea in both humans and animals. Unfortunately, the study of epidemiology, biology, and immunity of human rotaviruses has been hindered by the difficulties encountered in propagating these fastidious viruses in tissue culture. Recent studies indicate that at least some human rotavirus isolates may be cultivated directly (Wyatt et al, U.S. Pat. No. 4,341,870). As a strategy to circumvent the difficulties in cultivation encountered with human rotavirus, this invention has taken advantage of the segmented nature of the rotavirus genome and its high frequency of gene reassortment during coinfection to rescue non-cultivatable human rotaviruses by reassorting them with a cultivatable temperature-sensitive (ts) mutant of a bovine rotavirus. In conjunction with the use of the ts mutant, an excess of high titer hyperimmune antisera was utilized. The genes of the noncultivatable human rotavirus that restricted growth in vitro were replaced by the corresponding genes from the tissue culture-adapted bovine rotavirus. Viruses with reassorted genes are termed "reassortant viruses" or "reassortants."

It was thought initially that, in addition to the high titer antisera used to select the reassortants, temperature sensitive mutants were necessary to add selective pressure against the bovine parent (Greenberg et al, Proc. Natl. Acad. Sci. USA, Vol. 78, No. 1, pp. 420–424, January 1981). Initially, as is set out in the Greenberg article, selection of the desired viral reassortants was achieved by exposing progeny from mixed infection to potent specific bovine rotavirus antiserum that did not neutralize human rotavirus. Surviving virus was then plaqued at restrictive temperatures (39° C.) to eliminate the ts-bovine rotavirus parent and ts-reassortants.

In the present invention the use of temperature sensitive mutants is eliminated and reliance is placed upon the efficiency of the antisera which may be hyperimmune antisera, such as guinea pig, and, alternately, a monoclonal antibody selected from certain monoclonal antibodies as follows: 954/159/33; 954/96/18; and 952/3/68.

Of the first reassortants characterized from the human rotavirus strain D and bovine rotavirus UK mixed infection, 3 have 1 gene from human rotavirus strain D and 3 have 2 genes from human rotavirus strain D. In other words, the remainder of those genes of those reassortants come from the bovine UK parent.

Statement of Deposit

The following antibodies with cell lines described in this application as monoclonal antibodies 954/159/33, 954/96/18, and 952/3/68, were deposited in the Laboratory of the L.I.D., National Institute of Allergy and Infectious Diseases, Building 7, National Institutes of Health, Bethesda, Md. 20205. This depository has operated in standard fashion for comparable laboratories and is operated with a 70° C. storage in vapor liquid nitrogen freezing liquid and provides for sterile isolation of viable hybridoma cells and suspension of these cells in cryopreservative media and provides for thawing for regular inspection and viability tests. This depository is presently under the jurisdiction of Dr. Robert M. Chanock. These antibodies were deposited Mar. 18, 1982, and Apr. 5, 1982, and from that date until the filing date of this application were available to workers in the art requesting samples. Bovine rotavirus (NCDV) is a known virus available through the ATCC (#VR-452); see ATCC, Catalog of Strains II, 3d edition, p. 343 (1981). The following human/bovine reassortant rotavirus was deposited with ATCC on June 16, 1983, under ATCC #VR2069. This reassortant is human rotavirus serotype 1 but also contains bovine rotavirus UK genes. It is designated: HD/BRV-1, Clone 47-1-1, June 16, 1983.

Material Information Disclosure

Greenberg, Harry B., et al, "Rescue of Non-cultivatable Human Rotavirus by Gene Reassortment During Mixed Infection with ts Mutants of a Cultivatable Bovine Rotavirus," Proc. Natl. Acad. Sci. USA, vol. 78, No. 1, pp. 420–424, January 1981—Using the ts genes of bovine rotavirus, genes of fastidious rotaviruses that restricted growth in vitro were replaced by the corresponding genes from a tissue culture-adapted rotavirus.

Kalica, Anthony R., et al, "Genes of Human (Strain WA) and Bovine (Strain UK) Rotaviruses That Code for Neutralization and Subgroup Antigens," Virology, 112, 385–390 (1981)—Analysis of 16 rotaviral reassortants recovered from mixed infection with a ts mutant of bovine rotavirus (UK strain) and either non-cultivatable or cultivatable human rotavirus (WA strain) were analyzed and indicated that the ninth RNA segment codes for the protein that induces and reacts with neutralizing antibodies, the sixth RNA segment codes for the subgroup antigen, and probably the fourth RNA segment is responsible for restriction of growth of the noncultivatable human rotavirus in cell culture.

Flores, Jorge, et al, "Use of Transcription Probes for Genotyping Rotavirus Reassortants," Virology, 121, 288–295 (1982).

Greenberg, Harry B., et al, "Rescue and Serotypic Characterization of Noncultivable Human Rotavirus by Gene Reassortment," Infection and Immunity, Vol. 37, No. 1, pp. 104–109, July 1982—This article shows 33 of 50 noncultivatable human rotavirus strains which were successfully rescued by gene reassortment.

Kalica, Anthony R., et al, "Identification of the Rotaviral Gene That Codes for Hemagglutination and Protease-Enhanced Plaque Formation," *Virology*, 125:194–205, 1983 —Temperature-sensitive mutants of bovine rotavirus, UK Compton strain, and rhesus monkey rotavirus, MMU18006 strain, were used to derive 16 reassortants by coinfection in MA104 cells. It was found, among other results, that the neutralization antigen was linked to the eighth or ninth RNA segment and that hemagglutination (HA) was linked to the fourth RNA segment.

Greenberg, Harry, et al, "Serological Analysis of the Subgroup Protein of Rotavirus, Using Monoclonal Antibodies," *Infection and Immunity*, Vol. 39, No. 1, pp. 91–99, January 1983 —In this article Dr. Greenberg and his co-workers bring into focus the term rotavirus subgroup, which refers to the antigenic specificity associated with the protein product of the sixth gene. The product of the sixth rotavirus gene is the 42Kd major internal structural protein and the authors describe monoclonal antibodies which react specifically with 2 antigenically distinct subgroups. This protein is present in large amounts on the virion and can readily be detected with a variety of antigen assay systems including complement fixation, immune adherence hemagglutination assay (IAHA), radioimmunoassay (RIA), and enzyme-linked immunosorbent assay (ELISA).

Greenberg, Harry B., et al, "Gene Coding Assignments for Growth Restriction, Neutralization and Subgroup Specificities of the W and DS-1 Strains of Human Rotavirus, " *J. General Virology*, 64:313–324, 1983—In serotyping rotaviruses, it was found that the ninth gene segment of W virus and the eighth gene segment of DS-1 human rotavirus were associated with serotype specificity, while the sixth gene segment of W virus was associated with subgroup specificity.

Greenberg, Harry B., et al, "Production and Preliminary Characterization of Monoclonal Antibodies Directed at Two Surface Proteins of Rhesus Rotavirus," *J. Virology*, 47:267–275, 1983.—Due to the serotypic identity of rhesus rotavirus (RRV) with one of the three major human rotavirus serotypes, RRV was also scheduled as a gene donor in the human/animal rotavirus reassortment to prepare vaccine precursors. Studies show that of 36 monoclonal antibodies which reacted with 1 of the 2 major surface proteins of rhesus rotavirus, 3 were available which immunoprecipitated specifically the 38Kd outer capsid glycoprotein, the 8th or 9th gene product.

U.S. Pat. No. 3,992,522 Chanock et al.
U.S. Pat. No. 4,341,870 Wyatt et al.

In the related journal articles mentioned above, it was noted that as to a mixed infection with a mutant of bovine rotavirus UK strain and non-cultivatable human rotavirus WA strain, it was indicated that the ninth RNA segment codes for the protein that induces and reacts with neutralizing antibodies. In addition, it appears that the fourth RNA segment may be responsible for restriction of growth of rotavirus in cell culture. It was found that 33 of 50 non-cultivatable human rotavirus strains from a variety of locations were successfully rescued by gene reassortment and also that 19 strains resembled the previously characterized human rotavirus serotype WA, whereas 3 strains were serologically related to the DS-1 strain; 11 strains appeared to be serotypically distinct from WA and DS-1 strains and thus represented one or more new human rotavirus serotypes.

Utility Statement

The reassortant processes and products of this invention have present utility in producing vaccine precursors and vaccines for human rotavirus disease.

General Process

Animal rotaviruses that may be used as gene donors are bovine (UK), simian (MMU18006), canine (CU-1), murine, and avian. Human rotaviruses suitable for use with this invention are either used in the form of gnotobiotic calf feces, human stool suspension, or as passaged in African green monkey kidney (AGMK).

The procedure first involves pretreating the human and animal rotaviruses with trypsin. Since the human rotavirus is either non-cultivatable or poorly cultivatable, it is centrifuged onto a monolayer of AGMK cells. This step increases the amount of virus that enters the cell, or in other words, increases the multiplicity of infection. The AGMK cells are then coinfected with an animal rotavirus strain, allowed to grow for approximately 36 hours, then harvested and frozen. The virus yield from these coinfected cells is then treated with highly specific antisera, effectively neutralizing the animal rotavirus parent. In the process of establishing the conditions for reassortment, it was determined that hyperimmune antisera or monoclonal antibody should not have activity directed toward the fourth gene product of the animal parent. This step is most critical, for in this manner an amalgam of reassortants is reduced to only those reassortant viruses containing the selected human phenotype. Individual virus plaques are then picked after 4–7 days and thus purified to form a homogenous preparation and are ready to form vaccine precursors or vaccines.

THE INVENTION

The critical feature of this invention is the selection technique used to separate the reassortants. To date the problem centered on developing a means of selection of desired reassortant rotaviruses. Prior to this invention, the most recent procedure involved the use of temperature-sensitive mutants of bovine rotavirus. For a more detailed discussion see *PNAS*, Vol. 78, p. 420; and *Infection and Immunity*, Vol. 37, p. 104.

Briefly, the temperature-sensitive procedure involves coinfecting a cultivatable bovine rotavirus and a non-cultivatable human rotavirus at permissive temperature and culturing the yield of the coinfection at a temperature incompatable (restrictive) with growth of the bovine virus. Only those reassortants that contain the non-temperature sensitive gene segments of the bovine strain survive.

The present system uses non-temperature sensitive animal parent rotavirus, providing two advantages: (1) the animal rotavirus is not subject to chemical mutagenesis, therefore silent point mutations, often genetically unstable, are not present in the animal rotavirus genes present in the reassortants; and (2) fewer human rotavirus genes are present in reassortants prepared using non-temperature sensitive animal rotavirus parents than using temperature sensitive rotavirus.

The present invention differs from the temperature-sensitive selection technique by the use of nontemperature sensitive virus. Selection of the desired viral reassortants is achieved by exposing progeny from mixed infections of animal and human rotavirus to potent, specific animal rotavirus antiserum which neutralizes the animal parent. In this manner, viral reassortants were recovered that (1) grew to high titer in tissue culture; (2) produced plaques with high efficiency; (3) were characterized as being phenotypically human by neutralization with serotype specific human rotavirus antiserum; and (4) contained a small number of human rotavirus genes.

Specific Disclosure

Four animal rotavirus strains contribute the cultivatable gene segments to the reassortant strains:
(1) Bovine: strain UK, grown in calf kidney cells
(2) Simian: strain MMU18006 (rhesus), grown in African green monkey kidney cells and subsequently grown in DBS-FRhL-2 cells (US Patent 4,040,905)
(3) Canine: strain CU-1, grown in AGMK cells
(4) Murine: strain EW22348, grown in AGMK cells
Avian rotaviruses possess characteristics of the above viruses which indicate that the avian rotaviruses will also contribute genes.

The teachings of this invention are not limited to these four animal rotaviruses—the final form of a vaccine cannot be predicted because additional serotypes continually emerge as important causes of the disease.

Four strains of human rotavirus are used that represent four distinct serotypes defined by plaque reduction neutralization assay:
(a) D strain, serotype 1, used in the form of gnotobiotic calf feces
(b) DS-1 strain, serotype 2, used in the form of gnotobiotic calf feces
(c) P strain, serotype 3, used in the form of approximate 2% human stool suspension; it is noted that rhesus rotavirus (MMU18006) and canine rotavirus (CU-1) are also serotype 3 rotaviruses.
(d) ST4 strain, serotype 4, used in the form of approximate 2% stool suspension or grown in AGMK cells.
As with the animal rotaviruses, the listing of the human strains is not intended to limit the scope of this invention. As new serotypes of rotavirus are identified, new vaccines are easily developed using the process of this invention.

The human/bovine reassortant rotavirus is human rotavirus serotype 1 but also contains bovine rotavirus UK genes. It is designated: HD/BRV-1, clone 47-1-1, 16 June 1983.

Both animal and human rotaviruses to be used in reassortment are pretreated with about 0.5 $\mu$g/ml trypsin for 1 hour prior to inoculation of the cell cultures. The non-cultivatable or poorly cultivatable human rotavirus is centrifuged onto the monolayer cultures of AGMK cells. This procedure increases the amount of virus which enters the cells, or in other words, increases the multiplicity of infection. The AGMK cells are then coinfected with the appropriate animal rotavirus strain. The mixture of viruses is allowed to grow and reassort at 37° for approximately 36 hours. The infected cells are harvested and frozen after 1½ to 2 days. The virus yield from an infected culture is then incubated with trypsin (10 $\mu$g/ml) for 1 hour at 37° C., followed by an additional 1 hour incubation at 37° C. with 1:100 or 1:500 dilution of highly specific hyperimmune antiserum for the animal rotavirus strain. This effectively neutralizes the animal rotavirus parent. The treatment with antiserum is a most critical step and is discussed in more detail in the next paragraph. Individual virus plaques are picked 4 to 7 days later, thus purifying the virus to form a homogenous preparation. The plaque-purified rotavirus reassortants are characterized for genotype (defining which genes come from which parent) and for phenotype (defining serotype by plaque reduction assay). Purified virus preparations are amplified as seed suspensions and combined with the pharmaceutically appropriate medium to produce either vaccine precursors or live attenuated vaccines. The purified virus is serially passaged so that the resulting vaccine precursor is formed from a live attenuated virus.

Attenuation of the virus may be achieved by reassortment of animal and human genes; further attenuation may be achieved by repeated passages through African green monkey kidney cell culture. The virus is purified by plaque formation and the formed plaque may be dissolved or taken up in a suitable solvent by procedures known in the art to prepare a bacterially sterile preparation of live virus. The actual preparation of similar vaccines is taught in the section on Viral Vaccines, Remington's Pharmaceutical Sciences, 16th ed., 1980, pp. 1331-1335, published by the Philadelphia College of Pharmacy and Science and printed by Mack Printing Co., Easton, PA.

Monoclonal Antibodies and Hyperimmune Antisera

In reassortants derived from human non-cultivatable rotavirus and animal rotavirus parents, the key feature of the present invention is in the treatment of the progeny of mixed infection with neutralizating antibodies. This is done by using highly specific antibodies, which neutralize the animal rotavirus parent. In the case of simian (RRV) and canine (CU-1) rotaviruses, preferred antibodies consist of a pool of three separate antibodies directed at the 38 Kd glycoprotein of the simian rotavirus. These monoclonal antibodies cross-react effectively with high titer with the canine rotavirus and other type 3 viruses also. In the course of developing these monoclonal antibodies to rhesus rotavirus, it was found that only 3 of 39 monoclonal antibodies precipitated the critical 38 Kd outer capsid glycoprotein which is equivalent to the eighth or ninth gene product that induces or reacts with serotype specific neutralizing antibodies. In the case of bovine rotavirus (UK), cross reactive antiserum raised against the bovine rotavirus (NCDV) was used. This antiserum cross reacts effectively in high titer with the 38 Kd glycoprotein of bovine rotavirus (UK) but has little or no neutralizing activity directed at the 82 Kd protein of bovine rotavirus (UK).

As to neutralizing monoclonal antibodies, there are utilized in this invention 954/159/33; 954/96/18; and 952/3/68. These monoclonal antibodies may be utilized singly or in multiple applications. They are all targeted on precipitating the critical 38Kd outer capsid glycoprotein, which is equivalent to the eighth or ninth gene product which codes for the protein that induces or reacts with neutralizing antibodies.

Similarly, as to high titer hyperimmune antisera in this invention, this is selected from a high titer hyperimmune antiserum prepared in guinea pigs. It is noted that the monoclonal antibodies (noted above) were derived from monoclonal antibodies known and utilized at the time of the filing of the present application. It is further noted that conventionally this type of vaccine precursor involves the genetic reassortment and serial passage of known virus or known infectious virus so that the product is always a live, attenuated virus. As aforesaid, the precursor is in the form of a plaque which may be by conventional means utilized to prepare a bacterially sterile vaccine.

Hyperimmune antisera for the DS-1 strain of type 1 human rotavirus, the WA strain of type 2 human rotavirus and the NCDV (Lincoln) strain of bovine rotavirus were prepared in guinea pigs. The bovine and DS-1 rotaviruses were partially purified by sucrose-gradient centrifugation and administered in Freund's complete adjuvant. The tissue culture-adapted WA mutant of human rotavirus was partially purified by centrifugation through a sucrose cushion and also was administered in Freund's complete adjuvant. Three weeks later, virus was administered in Freund's incomplete adjuvant, followed in another 3 weeks by a final inoculation of virus without adjuvant. The type 1 human virus was purified from the stool of an infected gnotobiotic calf, whereas the type 2 human virus was grown in AGMK cell culture. The NCDV strain of bovine rotavirus was grown in AGMK cells.

Method of Testing

The selection of antibodies which would neutralize the animal rotavirus and immunoprecipitate the 38Kd glycoprotein (the 8th or 9th gene product) can be selected from those monoclones which will fill the above requirements by tests of immunoprecipitation and neutralization. In the Greenberg article, "Production and Preliminary Characterization of Monoclonal Antibodies Directed at Two Surface Proteins of Rhesus Rotavirus," to appear in *J. Virology*, 47:265-276, 1983, there is described a group of 39 antibodies, 36 of which immunoprecipitate the 82Kd outer capsid protein, the product of the 4th gene, the viral hemagglutinin. Of the 39, only 3 monoclonal antibodies were usable to neutralize rhesus rotavirus to high titer; the 3 also had HI activity. The 36 exhibited hemagglutination inhibition and neutralized rhesus rotavirus to moderate or high titer.

EXAMPLE 1

Neutralization Assay. Supernatant fluids from hybridoma cultures, ascites from mice inoculated with selected hybridomas, and preinoculation mouse sera, were titered in a standard 60% plaque reduction assay. Two hundred $\mu$l of virus activated with trypsin and representing 15 to 80 plaque forming units (PFU) was mixed with 200 $\mu$l of serial two-fold or four-fold dilutions (in MEM) of monoclonal antibody. After a one-hour incubation period at 37° C. the mixture was inoculated onto MA104 monolayers and allowed to adsorb for one hour. Wells were then washed once and overlaid with EMEM agarose. After 3-6 days an agarose overlay containing neutral red was added and the plaques counted. Negative controls included virus mixed with NS1 supernatant fluid and virus incubated with monoclonal culture fluid (HAT) and virus mixed with preinoculation mouse serum.

Results. Previous studies had shown that screening of monoclones by solid phase RIA led to the preferential selection of hybridomas directed at the major inner structural protein of rotaviruses, the 42Kd product of the 6th gene. An HI assay was therefore chosen as the primary screening procedure for the isolation of monoclonal antibodies directed at the surface proteins of RRV. From 1,000 wells initially screened by HI, 39 separate monoclonal antibodies with HI activity were eventually cloned and grown up in volume for further analysis.

Thirty-six of the thirty-nine monoclonal antibodies with HI activity precipitated an 82Kd protein from RRV cell lysates. In addition, these monoclonal antibodies precipitated 1 to 3 less intense bands in the 70-75Kd range. The monoclonal antibodies which precipitated the 82Kd protein were titered by HI against a variety of hemagglutinating rotaviruses. Each exhibited a high degree of homologous specificity in HI assay. Low level cross reactivity with monkey SA11 and porcine OSU rotaviruses was observed in a few instances. The monoclonal antibodies which immunoprecipitated the 82Kd protein were also assayed in a standard plaque reduction neutralization assay against RRV. Neutralizing activity was not detected in the supernatants of these monoclonal cell cultures tested at a 1:20 dilution. Because of the lack of detectable neutralizing activity in the hybridoma cell culture supernatant fluids, ascites fluids derived from mice inoculated with hybridoma cells which produce monoclonal antibodies to the 82Kd protein were tested by plaque reduction neutralizing. The HI titers versus RRV of the ascites fluid were between $10^2$ and $10^{3.5}$ fold higher than titers of the culture fluid supernate. Moderate to high levels of neutralizing activity was detected with the ascites fluid when studied in plaque reduction neutralization assay. The preinoculation serum neutralizing antibody titer of each of the mice against RRV was less than 1:500. In limited neutralization tests against heterologous viruses, the neutralizing activity appeared to be highly specific for the immunizing RRV strain. The neutralizing activity of these monoclonal antibodies was not affected by trypsin treatment of RRV at a concentration that enhances infectivity. A peculiar characteristic of the plaque reduction assay with the antihemagglutinin hybridomas was that a small fraction (10–20%) of virus was not neutralized by any of the concentrations of ascites fluid tested.

The 4th gene of RRV was identified as the gene which coded for the 82 Kd protein by reacting selected monoclonal antibodies which precipitated the 82 Kd protein with a variety of RRV X UK bovine rotavirus reassortants in solid phase RIA. Since these monoclonals reacted specifically with RRV in solid phase RIA but failed to bind to UK bovine virus, their binding to selected reassortants could be used to determine the gene origin of the 82 Kd protein. Both the genotype and phenotype of the reassortants studied had previously been determined. The UK bovine rotavirus parent does not hemagglutinate red blood cells while RRV does. Reassortants with a 4th gene derived from the RRV parent hemagglutinated RBC's while those reassortants in which the 4th gene was derived from the UK bovine rotavirus did not hemagglutinate. The monoclonal antibodies which precipitated the 82 Kd protein reacted in RIA only with those reassortants which contained a hemagglutinating protein, that is, reassortants that derived their 4th gene from the rhesus rotavirus. All other rotaviral genes could be excluded as coding for the protein which reacted with these monoclonal antibodies.

Of 39 monoclonal antibodies 3 had HI activity but did not precipitate the 82 Kd protein. These three monoclonal antibodies immunoprecipitated a 38 Kd band that migrated just ahead of the 42 Kd major inner structural protein of RRV. Experiments using tunicamycin treated cell lysates demonstrated that this band was glycosylated and that the nonglycosylated precursor protein was precipitated by the monoclonal antibodies in the tunicamycin treated lysate. Cell culture supernatant fluid from these three monoclonal antibodies inhibited hemagglutination by the RRV, canine rotavirus, and to a lesser extent SA-11. Unlike hybridomas directed at the 82 Kd protein, monoclonal cell culture supernatant fluid from these three hybridomas exhibited neutralizing activity against RRV (titer 1:160 to 1:320). Mouse ascites fluid derived from the three monoclonal antibodies exhibited high titer neutralizing activity against the homologous rhesus rotavirus. Unlike the monoclonal antibodies to the 82 Kd protein, these monoclonal antibodies also efficiently neutralized the serologically related canine and SA-11 rotaviruses. The P strain of human rotavirus which is also serologically related to RRV was neutralized by two of the three monoclonal antibodies. The serologically distinct bovine UK and human WA strains were not neutralized. At dilutions of 1:2000 or less the three monoclones to the 38 Kd glycoprotein effected complete neutralization of RRV (100% plaque reduction).

Since the monoclonal antibodies which immunoprecipitated the 38 Kd glycoprotein reacted specifically with RRV and not UK rotavirus in solid phase RIA, similar techniques could be used as were used for monoclonals which immunoprecipitated the 82Kd protein. In previous studies there was shown that serotype was primarily a function of the 8th or 9th RNA segment, while viral hemagglutinin was coded for by the 4th RNA segment. When tested in solid phase RIA, the monoclonal antibodies against the 38 Kd glycoprotein bound only to RRV X UK bovine rotavirus reassortants that were serotypically rhesus rotavirus, whether or not the reassortant hemagglutinated red blood cells. When the genotype of the reassortants was correlated with the monoclonal binding in solid phase radioimmunoassay, it was found that monoclonal antibody binding correlated with the presence in the reassortant of an 8th or 9th gene derived from rhesus rotavirus. These two genes could not be differentiated in the reassortants. These data indicated that the 38 Kd glycoprotein is the product of one of these two gene segments.

Because the monoclonal antibodies directed at the 38 Kd glycoprotein had HI activity but did not appear to bind to the viral hemagglutinin in $^{35}S$ labeled cell lysates or in solid phase RIA, the monoclonal antibodies were tested for their capacity to inhibit hemagglutination by selected reassortants. Monoclonal antibodies 954/159/33 and 952/3/68 which precipitated the 38 Kd protein and tracked to the 8th or 9th RRV gene product in RIA had HI activity only when the reassortants exhibited the rhesus rotavirus neutralization serotype.

EXAMPLE 2

Hyperimmune Guinea Pig Antisera. Antisera prepared against the bovine rotavirus and the human rotavirus (types 1 and 2) were highly specific when assayed by plaque reduction. The homologous titer of the bovine virus antiserum was at least 1000-fold higher than its titer against the type 1 tissue culture-adapted WA human rotavirus. This meant that the antiserum could be used to selectively neutralize virus with bovine antigenic specificity without affecting virus with type 1 human rotavirus specificity that might be present in the same suspension. The type 1 and 2 human rotavirus antiserum was also potent and specific. It is unique that potent antibovine (NCDV) antiserum only neutralizes the bovine rotavirus (UK) by interaction with 34-38 Kd protein and not the 82-88 Kd surface protein. In fact, the 82-88 Kd proteins of the 2 viruses are antigenically different as measured by neutralization.

In this specification and claims the definition of non-cultivatable human rotavirus includes poorly cultivatable human rotavirus.

We claim:

1. A method of preparing a reassortant virus comprising
combining a human non-cultivatable rotavirus with a cultivatable animal rotavirus and producing a reassortant and neutralizing the animal rotavirus with a suitable antibody specific for the 34-38Kd glycoprotein of an animal rotavirus strain.

2. A method for producing a rotavirus reassortant suitable for use as a vaccine precursor which consists essentially of
combining a non-cultivatable human rotavirus parent with a cultivatable animal rotavirus parent and selecting the yield of the coinfection in the presence of a selective antibody with high neutralizing titer which are monoclonal antibodies which neutralize the animal parent by antibody directed toward the 34-38Kd glycoprotein and
producing a reassortant containing human and animal genes with human rotavirus antigenic serotype in plaque-purified form suitable for vaccine.

3. The method of claim 2 wherein the human rotavirus parent is selected from one member of the group consisting of human rotavirus D strain, serotype 1; DS-1 strain, serotype 2; P strain, serotype 3; and ST4 strain, serotype 4.

4. The method of claim 2 wherein the animal rotavirus parent is selected from one member of the group consisting of bovine strain UK, simian strain MMU18006, and canine strain CU-1.

5. A method for producing a rotavirus reassortant suitable for use as a vaccine precursor which consists essentially of
combining a non-cultivatable human rotavirus parent with a cultivatable animal rotavirus parent and selecting the yield of the coinfection in the presence of a selective antibody with high neutralizing titer selected from hyperimmune antisera which neutralize the animal parent by antibody directed exclusively toward the 34-38Kd glycoprotein and
producing a reassortant containing human and animal genes with human rotavirus antigenic serotype in plaque-purified form suitable for vaccine.

6. The method of claim 5 wherein the human rotavirus parent is selected from one member of the group consisting of human rotavirus D strain, serotype 1; DS-1 strain, serotype 2; P strain, serotype 3; and ST4 strain, serotype 4.

7. The method of claim 5 wherein the animal rotavirus parent is selected from one member of the group consisting of bovine strain UK, simian strain MMU18006, and canine strain CU-1.

* * * * *